United States Patent
Doran et al.

(10) Patent No.: US 12,263,117 B2
(45) Date of Patent: Apr. 1, 2025

(54) PATIENT WARMING SYSTEM WITH MONITORING AND FEEDBACK CAPABILITY

(71) Applicant: Solventum Intellectual Properties Company, Maplewood, MN (US)

(72) Inventors: Daniel P. Doran, Minneapolis, MN (US); Jia Hu, Mounds View, MN (US); Vinod P. Menon, Woodbury, MN (US); Greg E. Schrank, Bloomington, MN (US); Winston T. Tan, Plymouth, MN (US); Trung Vu, Minneapolis, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1027 days.

(21) Appl. No.: 16/621,297

(22) PCT Filed: Jun. 20, 2018

(86) PCT No.: PCT/IB2018/054553
§ 371 (c)(1),
(2) Date: Dec. 11, 2019

(87) PCT Pub. No.: WO2018/235019
PCT Pub. Date: Dec. 27, 2018

(65) Prior Publication Data
US 2020/0113729 A1    Apr. 16, 2020

Related U.S. Application Data

(60) Provisional application No. 62/524,342, filed on Jun. 23, 2017.

(51) Int. Cl.
*A61F 7/02* (2006.01)
*A61B 5/021* (2006.01)
*A61F 7/00* (2006.01)

(52) U.S. Cl.
CPC .......... *A61F 7/02* (2013.01); *A61B 5/021* (2013.01); *A61F 7/007* (2013.01); *A61F 7/0085* (2013.01);
(Continued)

(58) Field of Classification Search
CPC .......... A61F 7/007; A61F 7/02; A61F 7/0097; A61F 7/0085; A61F 7/00; A61F 7/12;
(Continued)

(56) References Cited

U.S. PATENT DOCUMENTS

| 4,331,161 A | 5/1982 | Patel |
| 5,941,907 A * | 8/1999 | Augustine ............... A61F 7/00 607/104 |

(Continued)

FOREIGN PATENT DOCUMENTS

| WO | WO-2016069551 A1 * | 5/2016 | ............... A61F 7/02 |
| WO | WO 2017-002278 | 1/2017 | |

OTHER PUBLICATIONS

Akata, "Reliability of fingertip skin-surface temperature and its related thermal measures as indices of peripheral perfusion in the clinical setting of the operating theatre", Anaesth Intensive Care, 2004, vol. 32, No. 4, pp. 519-529.
(Continued)

*Primary Examiner* — Khadijeh A Vahdat
*Assistant Examiner* — Marina Delaney Templeton

(57) ABSTRACT

Aspects of the present disclosure provide for a patient warming system having a heating device configured to transfer heat to a patient based on a body heat score that indicates whether the patient is likely to sweat. The heating device includes a heater circuit configured to produce heat, the heater circuit thermally coupled to the patient. The heating device also includes a controller communicatively coupled to the heater circuit. The controller has one or more
(Continued)

processors configured to receive one or more physiological indicators of the patient, determine the body heat score from one or more physiological indicators, determine whether the body heat score meets a score threshold, direct the heater circuit to produce a first amount of heat based on whether the body heat score meets a score threshold.

15 Claims, 11 Drawing Sheets

(52) U.S. Cl.
CPC ............... *A61F 2007/0093* (2013.01); *A61F 2007/0096* (2013.01); *A61F 2007/0282* (2013.01)

(58) Field of Classification Search
CPC ............ A61F 7/08; A61F 2007/0282; A61F 2007/0096; A61F 2007/0093; A61F 2007/0054; A61F 2007/0288; A61F 2007/0088; A61F 2007/0059; A61F 2007/126; A61F 2007/0077; A61F 2007/0091; A61F 2007/0095; A61B 5/021; A61B 5/01; A61B 5/02055; A61B 5/6892; A61B 5/0816; A61B 5/024; A61B 5/746; A61B 5/0008; A61B 5/389; A61B 5/7275; A61B 2017/00084; A61B 2014/00044; A61B 2018/00095; H05B 2203/036; A41D 13/0051; A41D 13/1236; G16H 50/30; G16H 40/60
See application file for complete search history.

(56) References Cited

U.S. PATENT DOCUMENTS

| | | | |
|---|---|---|---|
| 6,173,197 B1 | 1/2001 | Boggett | |
| 6,263,227 B1 | 7/2001 | Boggett | |
| 6,319,205 B1 | 11/2001 | Goor | |
| 6,322,515 B1 | 11/2001 | Goor | |
| 6,337,993 B1 | 1/2002 | Kishida | |
| 6,544,180 B1 | 4/2003 | Doten | |
| 6,834,202 B2 | 12/2004 | Ono | |
| 7,361,186 B2 | 4/2008 | Voorhees | |
| 8,435,278 B2* | 5/2013 | Callister | A61F 7/007 607/104 |
| 2005/0103353 A1* | 5/2005 | Grahn | A61F 7/02 607/108 |
| 2009/0240312 A1* | 9/2009 | Koewler | A61F 7/0097 607/104 |
| 2010/0152822 A1* | 6/2010 | Callister | A61F 7/007 607/105 |
| 2011/0024076 A1 | 2/2011 | Lachenbruch | |
| 2013/0127689 A1 | 5/2013 | Gollier | |
| 2014/0277302 A1* | 9/2014 | Weber | A61F 7/0085 607/104 |
| 2015/0238350 A1* | 8/2015 | Tijs | A61F 7/00 607/104 |
| 2016/0016338 A1 | 1/2016 | Radcliffe | |
| 2016/0135987 A1* | 5/2016 | Mignot | A61F 7/0085 607/105 |
| 2017/0156923 A1* | 6/2017 | Utturkar | A61B 5/7278 |
| 2017/0354534 A1* | 12/2017 | Paradis | A61F 7/12 |
| 2018/0193185 A1* | 7/2018 | Thomas | A61F 7/007 |
| 2019/0029537 A1* | 1/2019 | Buller | A61B 5/11 |
| 2019/0104776 A1* | 4/2019 | Luoma | A41D 13/0053 |

OTHER PUBLICATIONS

House, "Using skin temperature gradients or skin heat flux measurements to determine thresholds of vasoconstriction and vasodilatation", European Journal of Applied Physiology, 2002, vol. 88, No. 1, pp. 141-145.
Hynson, "Heat storage capacity of the peripheral thermal compartment", Anesthesiology, 1991, vol. 75.pp. A195.
Rubinstein, "Skin-surface temperature gradients correlate with fingertip blood flow in humans", Anesthesiology, 1990; vol. 73, No. 3,pp. 541-545.
International Search report for PCT International Application No. PCT/IB2018/054553 mailed on Oct. 11, 2018, 4 pages.

* cited by examiner

PATENT WARMING SYSTEM WITH MONITORING AND FEEDBACK CAPABILITY

CROSS REFERENCE TO RELATED APPLICATIONS

This application is a national stage filing under 35 U.S.C. 371 of PCT/IB2018/054553, filed Jun. 20, 2018, which claims the benefit of U.S. Provisional Application No. 62/524,342, filed Jun. 23, 2017, the disclosures of which are incorporated by reference in their entirety herein.

BACKGROUND

Core body temperature is typically 2-4° C. warmer than peripheral tissues. This normal core-to-peripheral tissue temperature gradient is maintained by thermoregulatory vasoconstriction. Induction of general anesthesia inhibits vasoconstriction, allowing a core-to-peripheral redistribution of body heat. Because a flow of heat needs a temperature gradient, redistribution magnitude is limited when peripheral and core temperatures are similar. By pre-warming the peripheral tissues before anesthesia is induced, the amount of heat redistributed to the peripheral tissues is reduced thus reducing the chance of hypothermia and its associated complications.

Pre-warming to prevent Redistribution Temperature Drop (RTD) can be an effective strategy to prevent anesthesia-related hypothermia. Pre-warming can involve storing energy in the peripheral thermal compartments prior to the induction of anesthesia. Pre-warming can accomplished by heating the peripheral thermal compartment, which increases the Mean Body Temperature (MBT), but has minimal effect on the body's core temperature. Pre-warming can further decrease the temperature gradient that exists normally between the peripheral tissues and the core of a patient such that the core temperature of the patient has remains relatively consistent after anesthesia.

Mammalian patients may have internal thermoregulation mechanisms to tolerate temporary heat imbalances that allow the MBT to increase without mounting a significant thermoregulatory response. At a certain heat absorption, a mammalian body may respond by undergoing vasodilation, then, at a certain level of vasodilation, hidrosis or sweating. A mammalian body's short-term tolerance to heat imbalance is exploited during the prewarming period; however, once a patient begins to sweat, a significant portion of the energy stored in the peripheral thermal compartment is quickly lost to the environment and the advantage of prewarming disappears.

SUMMARY

Aspects of the present disclosure provide for a patient warming system having a heating device configured to transfer heat to a patient based on a body heat score that indicates whether the patient is likely to sweat. The heating device includes a heater circuit configured to produce heat, the heater circuit thermally coupled to the patient. The heating device also includes a controller communicatively coupled to the heater circuit. The controller has one or more processors configured to receive one or more physiological indicators of the patient, determine the body heat score from one or more physiological indicators, determine whether the body heat score meets a score threshold, direct the heater circuit to produce a first amount of heat based on whether the body heat score meets a score threshold.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application. In addition, one or more reference numbers may be first introduced in a figure of the application to refer to a device, a method step, or some other aspect related to the figure, wherein the same reference number may then be used in a subsequent figure or figures to refer to the same device, method step, or other aspect as described with respect to the original figure, but without a particular reference to the same reference numbers in the description corresponding to the subsequent figure(s). In such instances and unless stated otherwise, the reference numbers as used in the subsequent figure or figures incorporate all of the features, functions, and the equivalents thereof of the devices, method steps, or other aspects described with respect to the reference number where first introduced and described.

DETAILED DESCRIPTION

Current prescription of pre-warming using forced air warming is to set a heating unit on 'high temperature' for a predetermined time. There is no input information from the patient to adjust the temperature of the hardware unit according to the patient's condition.

Thus, there remains a need for a patient warming system that can determine when a patient is likely to sweat and control a heating device based on the likelihood of the patient to sweat.

Aspects of the present disclosure relate to a patient warming system having a heating device with a controller that determines an amount of heat to transfer to a patient and directs a heater circuit to produce the amount of heat. Various aspects of the present disclosure may relate to a controller that receives one or more physiological indicators from a patient and uses the one or more physiological indicators determine the amount of heat produced by the heater circuit such that the patient does not sweat.

Figure 1:
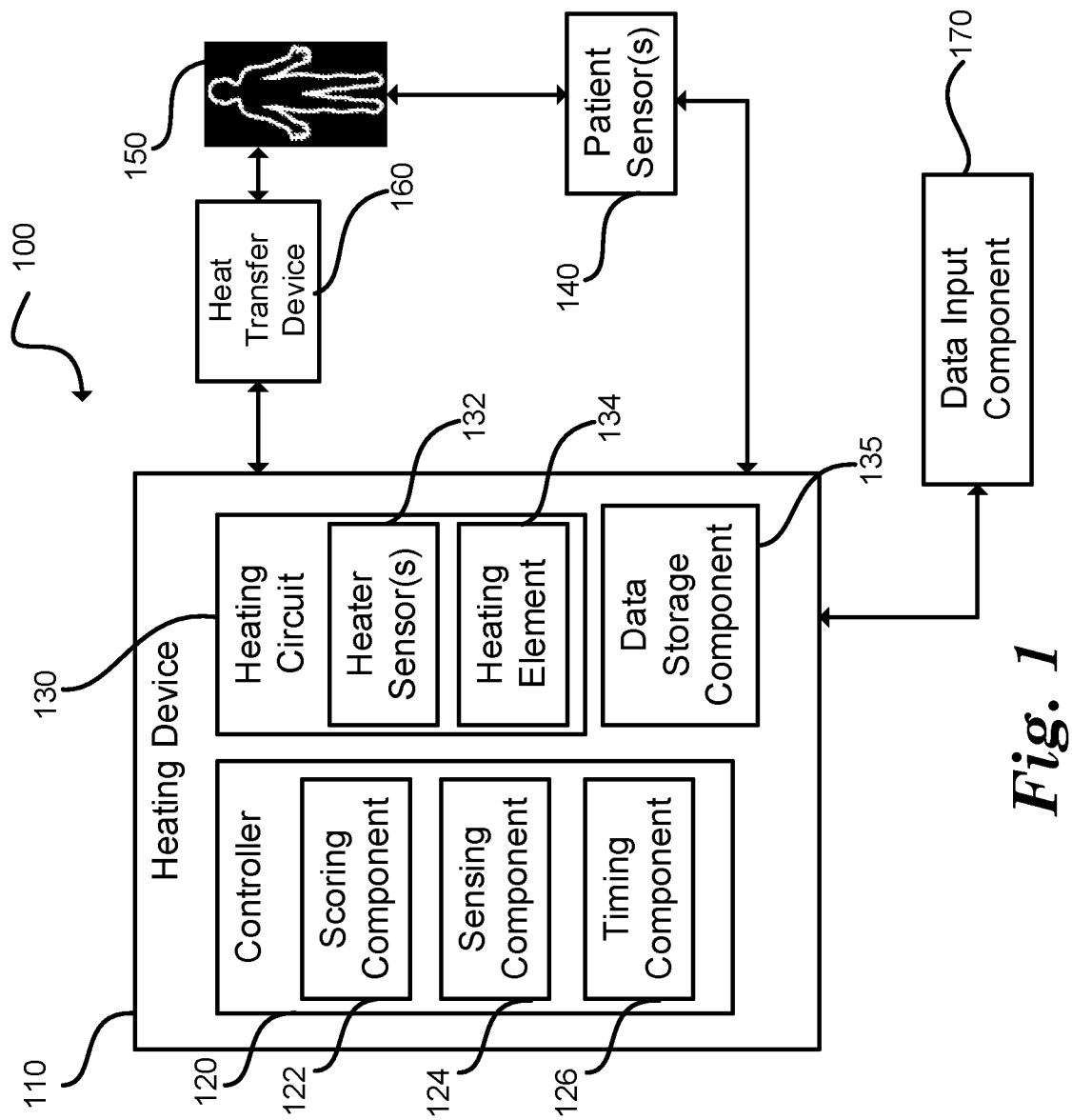
FIG. 1 illustrates a block diagram of an example patient warming system according to various techniques described in this disclosure.

FIG. 1 illustrates a patient warming system 100. The patient warming system 100 can include a heating device 110, one or more patient sensors 140, a heat transfer device 160, and data input component 170.

The heating device 110 can control an amount of heat applied to a patient 150. In some embodiments, the patient 150 is a homoeothermic animal species that can undergo hidrosis (i.e., preferably a human, but also including another primate or equine species).

The heating device 110 can preferably be a convection heater (e.g., that relies on blown air over a heating element). The heating device 110 can also be a fluidic heater (e.g., that uses a heater circuit 130 to heat fluid which transfers heat to the patient 150), or a conductive heater (e.g., that relies on electrical current through a heating circuit 130 to be apply heat conductively to a patient).

The heating device 110 can apply heat to the patient 150 through an optional heat transfer device 160. The heat transfer device 160 can disperse heat from the heating device 110 onto the patient 150 such that the patient 150 does not received concentrated heat. In at least one embodiment, the heat transfer device 160 can be a pad, gel, catheter, fluid (such as an IV fluid warmed using a device under the trade designation Ranger from 3M (Saint Paul, MN)) or even a blanket such as those commercially available under the trade designation Bair Hugger from 3M (Saint Paul, MN). In at least one embodiment, the heat transfer device 160 can apply an amount of heat to at least 10%, at least 20%, at least 30%, at least 40%, at least 50%, or at least 60% of a total surface area of the patient 150.

In at least one embodiment, due to the lag time between heat transfer by a convection heater and absorption by the patient, detecting heat using physiological indicators from sensors can be useful. For example, the one or more patient sensors 140 can be configured to read one or more physiological indicators from the patient 150. In at least one embodiment, the patient sensor 140 can receive a physiological indicator from the patient 150. The physiological indicator can be a physiological response by the patient 150 to the amount of heat provided by the heating device 110. The patient sensors 140 are described further herein.

In at least one embodiment, entered physiological indicators can be received from a data input component 170. The data input component 170 can be a computer, keyboard, touch screen, or other input device that allows the heating device 110. In at least one embodiment, the data input component 170 can be a healthcare database accessed via a network communication device such as wireless internet or Ethernet.

The entered physiological indicators can differ from physiological indicators received by the sensor due to the sampling rate. For example, an entered physiological indicator is less likely to be measured more than once daily. Some entered physiological indicators such as body fat percentage or weight can also be measured by a sensor in addition to being entered. One way to define an entered physiological indicator can be a physiological indicator that is measured no more than twice during a 1 hour period. A sensor-based physiological indicator can be measured more than twice during a 1 hour period. Thus, some physiological indicators such as temperature will be measured more frequently than other physiological indicator such as height. Throughout this disclosure, the term physiological indicator can refer to either entered physiological indicators and or sensor-based physiological indicators.

In at least one embodiment, the heating device 110 can have a data storage component 135 that receives and stores one or more physiological indicators (entered or received from a sensor) for the patient 150. The one or more physiological indicators include information relevant to thermogenesis and thermolysis of the patient 150.

The controller 120 is a control element of the heating device 110. The controller 120 controls a heating circuit 130. For example, the controller 120 can direct the heating circuit to pause or produce a lower level of heating. In at least one embodiment, the controller 120 can control the heating circuit 130 based on a reading from a patient sensor 140. The controller 120 is communicatively coupled to the heating circuit 130, and the patient sensors 140. In at least one embodiment, the controller 120 is communicatively coupled to the heat transfer device 160.

The controller 120 can have one or more components that may be helpful to perform various functions described herein. For example, the controller 120 can have a scoring component 122, a sensing component 124, or a timing component 126, or combinations thereof.

A scoring component 122 can create a numerical score representative of a number of physiological indicators of a patient 150 and the respective weights of each physiological indicator. The one or more physiological indicators of the patient 150 can be received by the one or more sensors 140. The score can indicate when a patient 150 is likely to sweat. In at least one embodiment, the score can indicate the amount of heat transferred to and/or received by the patient 150. In at least one embodiment, the score can also factor thermogenesis of the patient 150. For example, the score can exclude thermogenesis of the patient 150.

The sensing component 124 can receive physiological indicators of the patient 150 from the one or more patient sensors 140. The sensing component 124 can be communicatively coupled to the scoring component 122.

The timing component 126 can be communicatively coupled to the heating circuit 130 and one or more patient sensors 140. The controller 120 can utilize the timing component 126 to determine the duration of the heat transfer to the patient 150 and to determine when physiological indicators from the patient sensors 140 are received relative to the duration of the heat transfer. For example, the controller 120 can determine when a patient fingertip temperature was measured and the rate of change of the fingertip temperature can factor into a score from the scoring component 122. In at least one embodiment, the controller 120 can use the duration of the heat transfer to determine when to deactivate a heating circuit 130.

The heating device 110 can have a heating circuit 130. The heating circuit 130 is a device that generates heat from electricity. The heating circuit 130 can cause the patient 150 to receive conductive, convective, irradiated, or inductive heat. In at least one embodiment, the heating circuit 130 is convective where a heating element and air blower work in conjunction to allow warmed air to contact the patient. In at least one embodiment, the heating circuit 130 can be a heating pad where a heating element directly heats a portion of the patient 150.

The heat generated from the heating circuit 130 can be transferred to the patient 150. The heating circuit 130 can also have one or more heater sensors 132 configured to sense the temperature of the heat output by the heating circuit 130. The one or more heater sensors 132 can be used to regulate the heat output by the heating circuit 130. For example, if a heater sensor 132 senses that temperature is over 37° C., then the heater circuit 130 can reduce the electrical current applied to a heating element 134. The heating circuit 130 can have multiple heating levels which correspond to different temperatures of the heating element 134.

Figure 2:
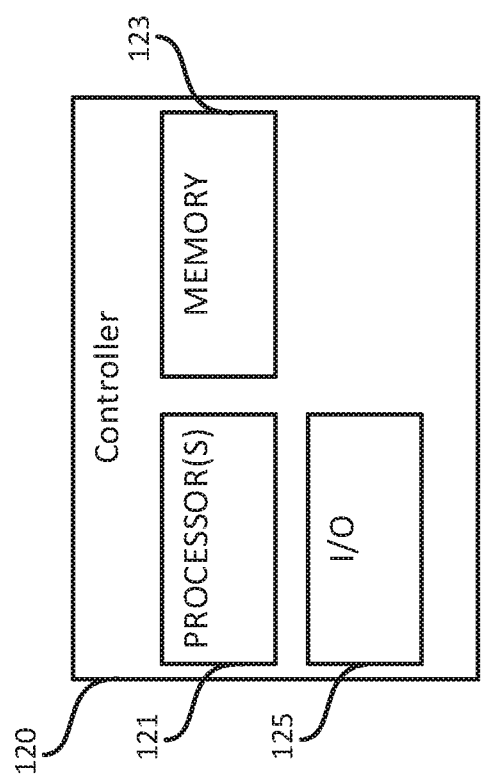
FIG. 2 illustrates a block diagram of an example controller of the patient warming system, according to various techniques described in this disclosure.

FIG. 2 illustrates a block diagram of some of the hardware aspects of the controller 120 including one or more processors 121, memory 123 and input/output (I/O) circuitry 125. Aspects of the controller 120 can be performed by one or more processors 121. For example, the one or more processors 121 can receive physiological indicators from a patient 150 (via the one or more patient sensors 140) and determine when to deactivate or cycle the heating circuit 130. The physiological indicators can be stored in the memory 123 until processed by the processor 121. The controller 120 can also include input/output (I/O) circuitry 125 to communicate with external devices such as data input components 170, displays, or the one or more patient sensors 140.

Figure 3:
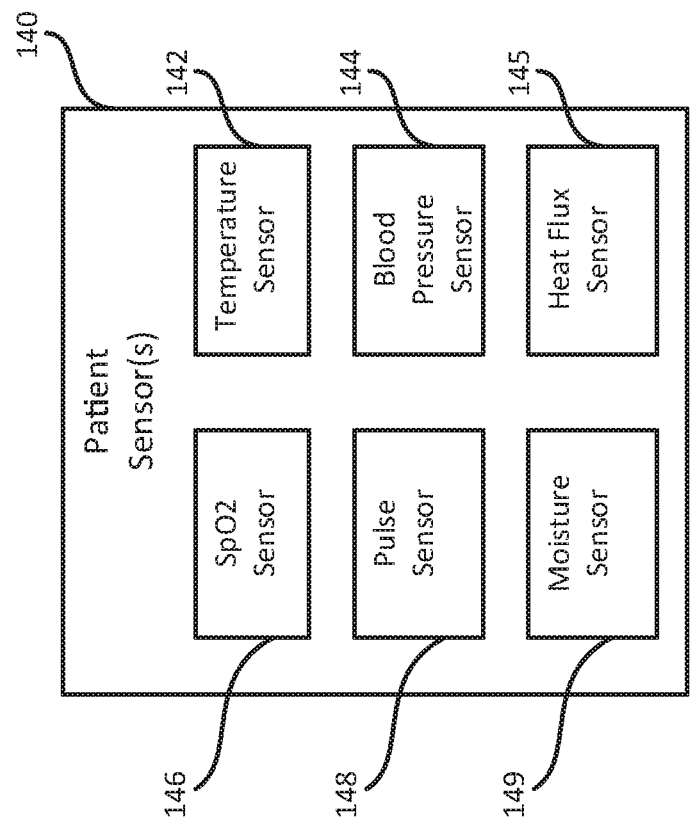
FIG. 3 illustrates a block diagram of exemplary patient sensors of the patient warming system, according to various techniques described in this disclosure.

FIG. 3 illustrates various patient sensors 140 that may be useful for monitoring physiological indicators of a patient 150. Either one patient sensor 140 or a plurality of patient sensors 140 can be used. The patient sensors 140 can include a temperature sensor 142, a blood pressure sensor 144, a heat flux sensor 145, a SpO2 sensor 146, a pulse sensor 148, a moisture sensor 149, or any combination thereof.

One or more temperature sensors 142 can be present in any location in the patient 150 and sense skin temperature or core temperature. In some embodiments, a zero-flux temperature sensor can be advantageous in measuring core temperature such as those commercially available under the trade designation SpotOn by the 3M Inc. (MN).

In at least one embodiment, the temperature sensor 142 can be located at the forearm (i.e., midway between the elbow and wrist joints), palms, fingertip (i.e., a pad between a distal inter-phalangeal joint and the distal end of a finger), forehead, or any combination therein of the patient 150. For example, the temperature sensors 142 can monitor a temperature differential between palms and a fingertip using two separate temperature probes with adhesive, two probes arranged in one adhesive strip, or two probes made in a hand mitten and connected finger cap, or any other physical means to held two probes in place without adhesive. Further, the one or more temperature sensors 142 can be located on the skin surface or implanted intravenously or rectally.

The blood pressure sensor 144, SpO2 sensor 146, pulse sensor 148, moisture sensor 149 can be used with the temperature sensor 142 to allow the controller 120 to determine whether a patient 150 is likely to sweat. For example, the controller 120 can use a temperature sensor 142 combined with moisture sensor 149 (to detect perspiration) to determine whether the patient 150 is likely to sweat. In another example, a rapid decrease (over a time period) in a blood pressure measurement can indicate vasodilation and the lack of body temperature increase can indicate that a patient 150 is likely to sweat.

Figure 4:
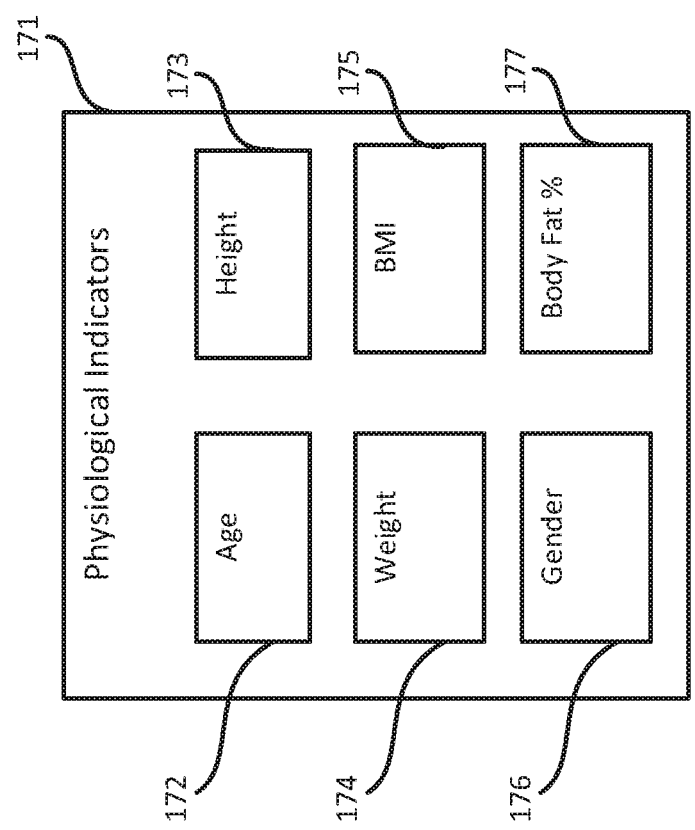
FIG. 4 illustrates a block diagram of an exemplary physiological indicators used by the patient warming system, according to various techniques described in this disclosure.

FIG. 4 illustrates a block diagram of entered physiological indicators 171. In various embodiments, the entered physiological indicators 171 can be entered from a data input component as opposed to provided by a sensor. The entered physiological indicators 171 can be the age 172, height 173, weight, 174, body mass index (BMI) 175, gender 176, or body fat percentage 177 of the patient, or combinations thereof. In at least one embodiment, another physiological indicator 171 can be the time duration that a patient needs to be warmed sufficiently in order to be ready for a clinical procedure.

Figure 5:
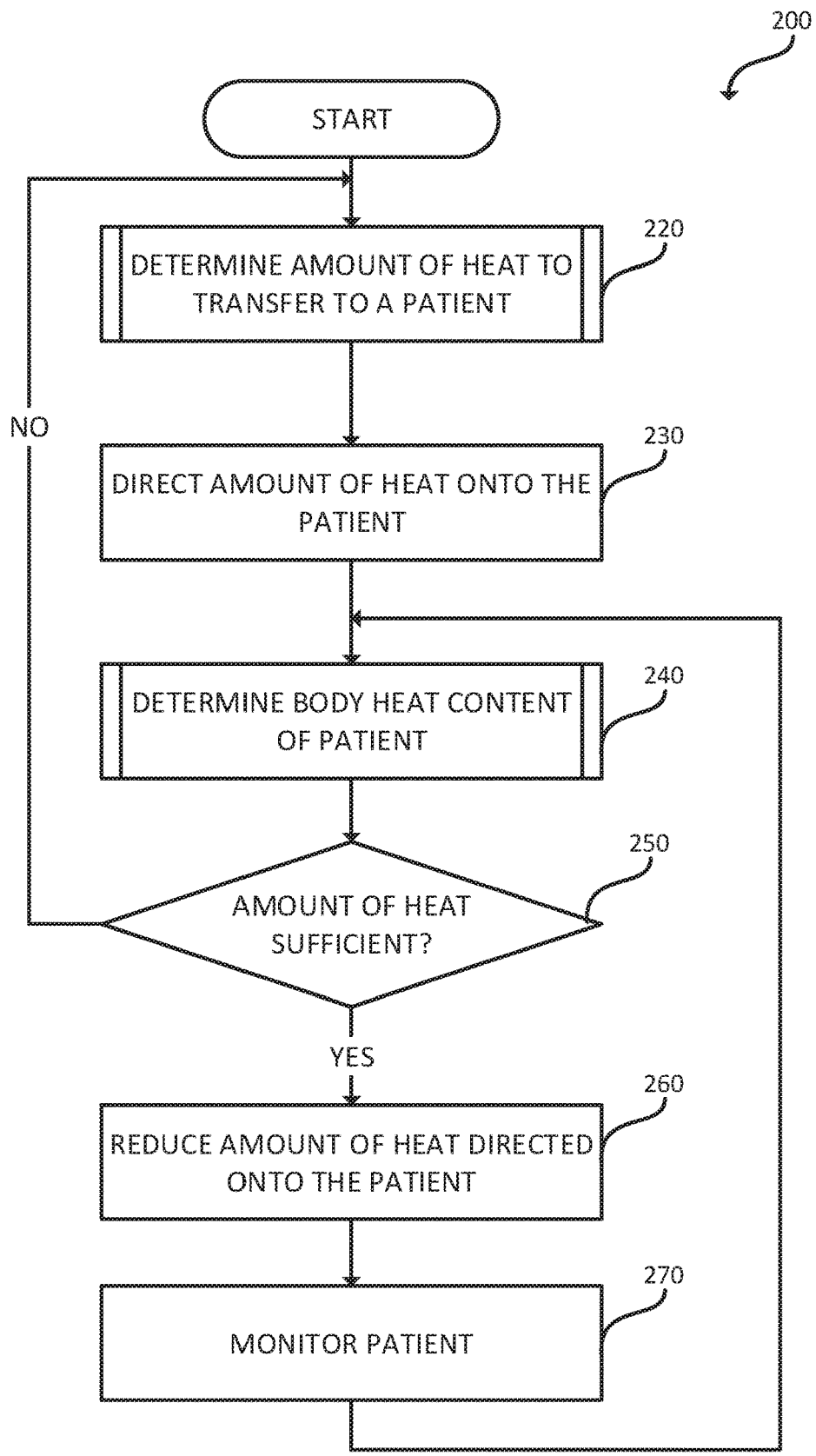
FIG. 5 illustrates a flowchart of an exemplary method for applying heat to a patient, according to various techniques described in this disclosure.

FIG. 5 illustrates a flowchart of a method 200 for heating a patient. The method 200 may refer to components found in the patient warming system 100. As discussed, various blocks can be optional depending on the configuration of the patient warming system 100. For example, in at least one configuration, the controller 120 of heating device 110 can be configured to apply an amount of heat to a patient based on entered physiological indicators. In other configurations, the entered physiological indicators can be optional and the controller 120 can be configured to adjust the amount of heat transferred to the patient based on physiological indicators obtained from the sensors 140 coupled to the patient 150 in response to a first amount of heat applied to the patient 150.

The method 200 can begin at block 220. In block 220, the controller 120 can determine the initial amount of heat to transfer to the patient. The initial amount of heat can be a numerical value such as a joule, or calorie. The controller 120 can receive one or more physiological indicators such as those described in FIG. 4. Once received, the controller 120 can determine an amount of the heat to transfer based on the one or more entered physiological indicators as described further herein. In at least one embodiment, the initial amount of heat can be an estimate of the amount of heat to sufficiently warm a patient. The method 200 can continue to block 230.

In block 230, the controller 120 can direct the heating circuit 130 to produce the initial amount of heat determined in block 220. The controller 120 can also account for the heat transfer rate or the effective heat transfer rate of the heating circuit 130 or heat transfer device 160. For example, if a convective heating device has a maximum heat transfer rate of 100 watts/sec but a patient receives an effective heat transfer rate of 40 watts/sec, then the controller 120 can utilize the effective heat transfer rate to determine the duration of time to direct the heating circuit 130 to produce the heat.

In block 240, the controller 120 can determine the body heat content of the patient. As described further herein, the body heat content of the patient 150 can be determined based on one or more physiological indicators from the patient 150 which can be measured from one or more patient sensors 140 (which are communicatively coupled to the patient 150 and the controller 120). The controller 120 can determine one or more physiological scores from one or more physiological indicators from the patient 150. In addition, a body heat score can be determined from the one or more physiological scores.

In block 250, the controller 120 can determine whether an amount of heat is sufficient to increase the body heat content of the patient 150 without causing the patient 150 to sweat. In at least one embodiment, the body heat score of the patient 150 can be compared to a score threshold. The score threshold is predetermined numerical value that indicates whether a patient is vasodilated and/or whether a patient is likely to sweat. The score threshold can be determined experimentally across multiple patients and is compared to the body heat score. If the score threshold is not met, then the amount of heat transferred by the heating device 110 is not sufficient. If the amount of heat transferred by the heating device 110 is not sufficient, then the method can continue to block 220 where the controller 120 can determine another amount of heat to transfer to the patient 150.

In at least one embodiment, the heating device 110 can be configured to have multiple heating levels. For example, the heating device 110 can have a high heating level, a maintenance heating level, and a reduced heating level. The controller 120 can direct the heating circuit 140 to use a heating level based on the body heat score. For example, the heating circuit 140 can operate at the high heating level because the patient 150 is vasoconstricted, at a maintenance heating level because the patient is vasodilated and pre-warming is sufficient, or at a reduced heating level because the patient 150 is likely to sweat if more heat is transferred.

In at least one embodiment, the controller 120 can determine whether the score threshold is met. In at least one embodiment, the score threshold can be met by the body heat score when the body heat score is greater than the score threshold. For example, if the score threshold is 45 and the body heat score is 65, then the score threshold is met. In at least one embodiment, the score threshold can be met when the score is increasing over a certain percentage. For example, if the score is increasing by 3% and the score threshold is 2%, then the score threshold can be met.

If the amount of heat is sufficient, then the controller can reduce the amount of heat directed onto the patient 150 in block 250. In at least one embodiment, the controller 120 can direct the heating circuit 130 to turn off or pause in block 260. In at least one embodiment, the controller 120 can direct the heating circuit 130 to maintain a heating level that is lower than the heating level determined in block 220.

The heating level reduction can be responsive to the body heat content of the patient 150. For example, a patient 150 with a first body heat score can result in the controller 120 turning off the heating circuit 130, whereas a patient 150 with a second body heat score that is lower relative to the first body heat score can cause the controller to maintain a lower heating level. In at least one embodiment, the lower heating level can be maintained for a certain time period, for example, no greater than 40 minutes, no greater than 30 minutes, no greater than 20 minutes, no greater than 10 minutes, or even no greater than 5 minutes. In at least one embodiment, the heating level can be relative to the heating capacity of the heating element 134. For example, the lower heating level can operate at no greater than 70%, no greater than 60%, no greater than 50%, or no greater than 40% of the heating capacity of the heating element 134.

After block 260, the method 200 can stop depending on the body heat score. In various embodiments, the controller 120 can optionally continue to monitor the patient in block 270.

In block 270, the controller 120 can continue to monitor one or more physiological indicators from the patient 150. For instance, the controller 120 can receive one or more physiological indicators from the one or more sensors 140. After monitoring the patient, the method 200 can continue to block 240 where the body heat content of the patient is determined using the data obtained in block 270.

Figure 6:
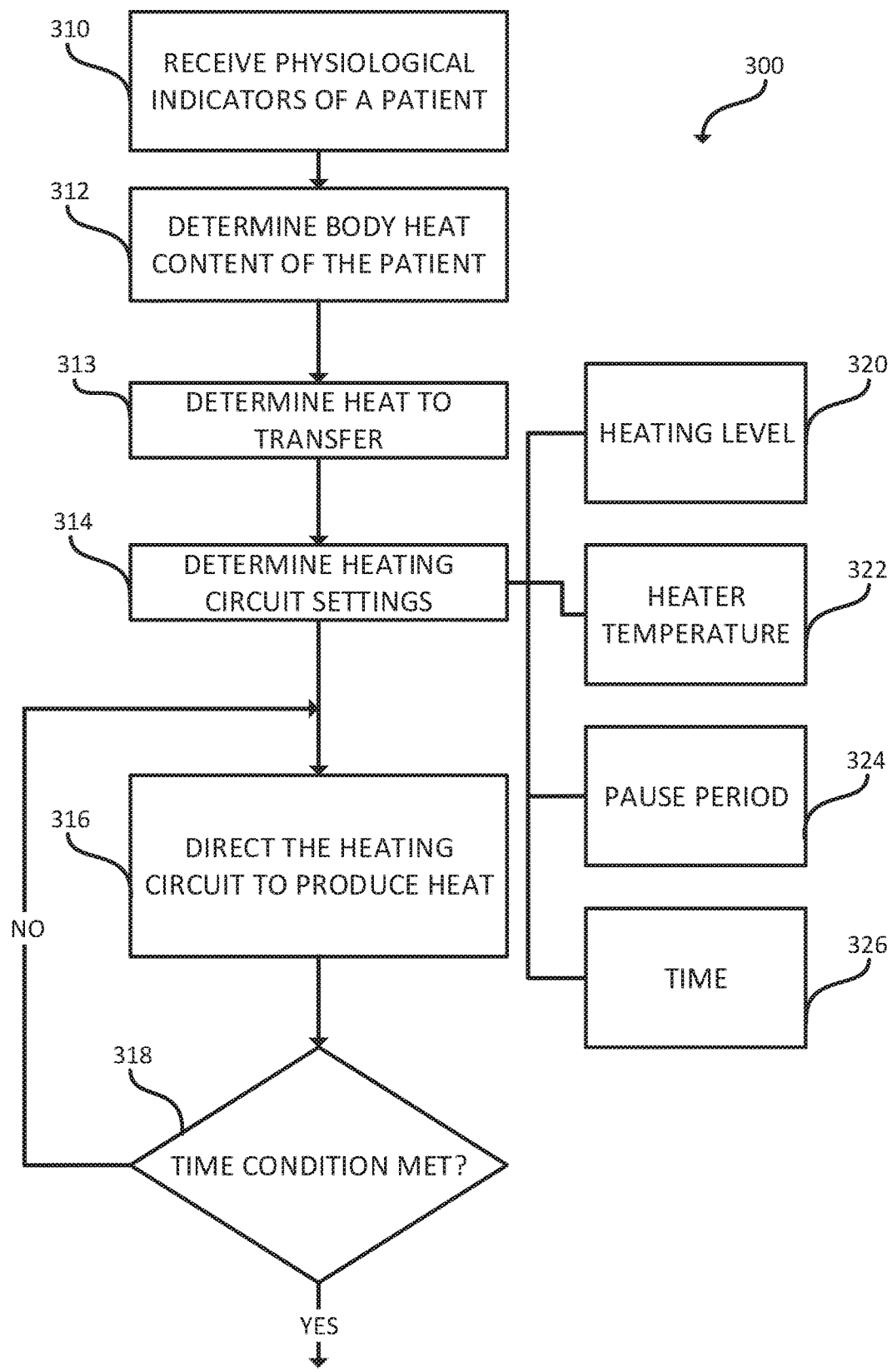
FIG. 6 illustrates a flowchart of an exemplary method for determining an amount of heat to apply to a patient, according to various techniques described in this disclosure.

FIG. 6 illustrates a method 300 for determining an amount of heat to apply to a patient 150, according to various embodiments. Aspects of method 300 can correspond to block 220 in FIG. 5. The method 300 can generally include receiving one or more entered physiological indicators of a patient 150 and determining the amount of heat to transfer based on the one or more physiological indicators. The method 300 can begin at block 310.

In block 310, the controller 120 receives one or more physiological indicators (e.g., from a data input component 170).

In block 312, the controller 120 can determine the body heat content of the patient. In at least one embodiments, the body heat content refers to the internal thermal energy of a body of a patient 150. Body heat content can be a function of at least body volume, body mass ratio, body specific heat and mean body temperature. The body heat content can be estimated using the entered physiological indicators received in block 310. In at least one embodiment, body heat content with an increased likelihood of causing hidrosis can be determined experimentally and accessible to the controller 120. In at least one embodiment, the body heat content can be further measured by measuring responses (such as an infrared camera) to known amounts of heat.

In block 313, the controller 120 can determine the amount of heat to transfer to the patient. For example, the heat to transfer can be a difference between a target body heat content and the body heat content determined in block 312.

In another example, the heat to transfer is the product of specific heat of the patient (which is a function of volume and body mass of the patient) and the difference between the final temperature and the initial temperature of the patient 150.

The efficiency of a heat transfer device 160 can also be considered. For example, a heat supplied equals the product of a determined heat to transfer and the efficiency of the heat transfer device 110.

In block 314, the controller can determine settings of heating circuit in 130 to supply the heat determined in block 312. For example, if a convective heating device has a maximum heat transfer rate of 100 watts/sec but a patient receives an effective heat transfer rate of 40 watts/sec, then the controller 120 can utilize the effective heat transfer rate to determine the duration of time to direct the heating circuit 130 to produce the heat.

For example, the specific heat of the body can be estimated based on body fat percentage and weight of the patient. The body heat content can be determined from the body mass and specific heat of the body and the applied or effective heat absorption of the patient. Thus, the controller 120 can determine the amount of heat that will raise the body heat content of the patient.

By comparing the amount of heat raises the body heat content of the patient with an empirically determined rate of heat transfer to the patient of the same or similar physiological indicators, a duration of heating can be determined and thus the heating device can be programmed.

In block 314, the controller 120 can determine the heating device 110 settings. For example, the heating circuit 130 can have one or more heating levels 320 (which reflect the amount of electrical current flowing through the heating circuit 130). The heating circuit 130 can also know the heating level 320 that will result in a particular heater temperature 322 (verified by the heater sensor 332).

If there is a pause period 324 where no heat is produced (such as in block 260 in FIG. 2), then the controller 120 can determine the relative heat retention by one or more components of the patient warming system 100. Also, the controller 120 can determine the amount of time 326 the heating circuit 130 is spent in the pause period 324 or reduced heating level.

In block 316, the controller 120 can direct the heating circuit 130 to produce heat using the heating circuit settings determined in block 314. For example, a convective heating circuit can utilize fan speed, heater temperature at a particular time to deliver a known amount of heat.

In block 318, the controller 120 can determine whether a time condition is met. For example, the controller 120 can determine whether the time 326 duration has elapsed. The time condition can be a heating circuit setting as shown in block 326. In at least one embodiment, the time condition 326 at a given heat transfer rate 328 can give an estimate of the amount of heat transferred to the patient 150. Any heat delivered past this time condition 326 may cause the patient 150 to receive excess amounts of heat.

If the time duration has not elapsed, then the method 300 can continue to block 316. In at least one embodiment, if the time duration has not elapsed, then the controller 120 can keep the current heating circuit settings or change the heating circuit settings (e.g., reduce the heating level of the heating element).

Figure 7:
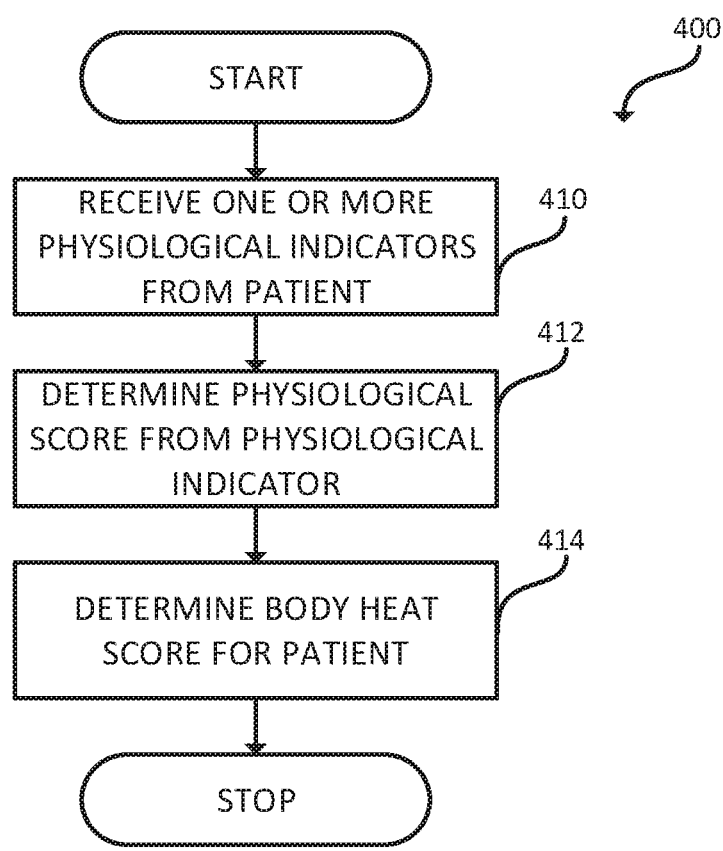
FIG. 7 illustrates a flowchart of an exemplary method for determining whether an amount of heat is sufficient, according to various techniques described in this disclosure.

FIG. 7 illustrates a flowchart of a method 400 for determining the body heat content of a patient 150. The method 400 can correspond to block 240 in FIG. 5. The method 400 can include receiving one or more physiological indicators from a patient in substantial real-time (meaning within 1 minute of collection) and using the one or more physiological indicators to determine a physiological score. The physiological score indicates a likelihood of the physiological indicator of causing the patient to sweat. In at least one embodiment, the one or more physiological scores can be weighted and aggregated into a body heat score. The body heat score can be representative of the likelihood of a patient to sweat.

The method 400 can begin at block 410. In block 410 the controller 120 can receive one or more physiological indicators from a patient 150. Preferably, the controller 120 can receive one or more physiological indicators from one or more sensors 140 communicatively coupled to the patient 150. The controller 120 can select or exclude data originating from one or more sensors. In some embodiments, the data originating from the one or more sensors can be filtered prior to being processed by the controller 120. For example, a fingertip temperature can filter temperatures greater than 45° C. After the physiological indicators are collected, then the method 400 can continue to block 412.

In block 412, the controller 120 can utilize the one or more of the physiological indicators to determine a physiological score for the patient 150. The physiological score can be a numerical representative of a physiological indicator and the likelihood of the physiological indicator to cause the patient 150 to sweat.

In at least one embodiment, the physiological score includes a fingertip temperature of the patient. For example, the fingertip temperature of the patient within 5% of 37° C. can indicate whether a patient is likely to sweat.

In at least one embodiment, a rising or falling physiological indicator can also be included in the physiological score. The degree of rise or fall can be included. For example, if three fingertip temperatures are sequentially taken, then a first, a second, or a third temperature can be taken. If the difference between the second and third temperature is less than the difference between the first and second temperature (indicating a leveling off of temperature increases), then the physiological score can be increased.

In block 414, the controller 120 can determine a body heat score for the patient. The body heat score can be a numerical representation of a body heat content of the patient and the likelihood of the patient to sweat. For example, the body heat score can indicate that the patient has absorbed heat and is unlikely to absorb more without sweating.

In at least one embodiment, the body heat score can be weighted. Various physiological scores can be weighted. For example, a difference between the fingertip and forearm temperature can be given a numeric score (e.g., a difference of under 4° C. can be given a score of 9 out of 10) and then weighted based on the level of correlation between fingertip and forearm temperature.

In at least one embodiment, the body heat score can be determined from a lookup table from values equaling particular physiological scores. In at least one embodiment, the body heat score can be determined from a single physiological score. For example, a core body temperature can produce a body heat score with a direct correlation. For example, the core body temperature can be the body heat score. In another example, the core body temperature above 36° C. can have a body heat score of 36.

Figure 8:
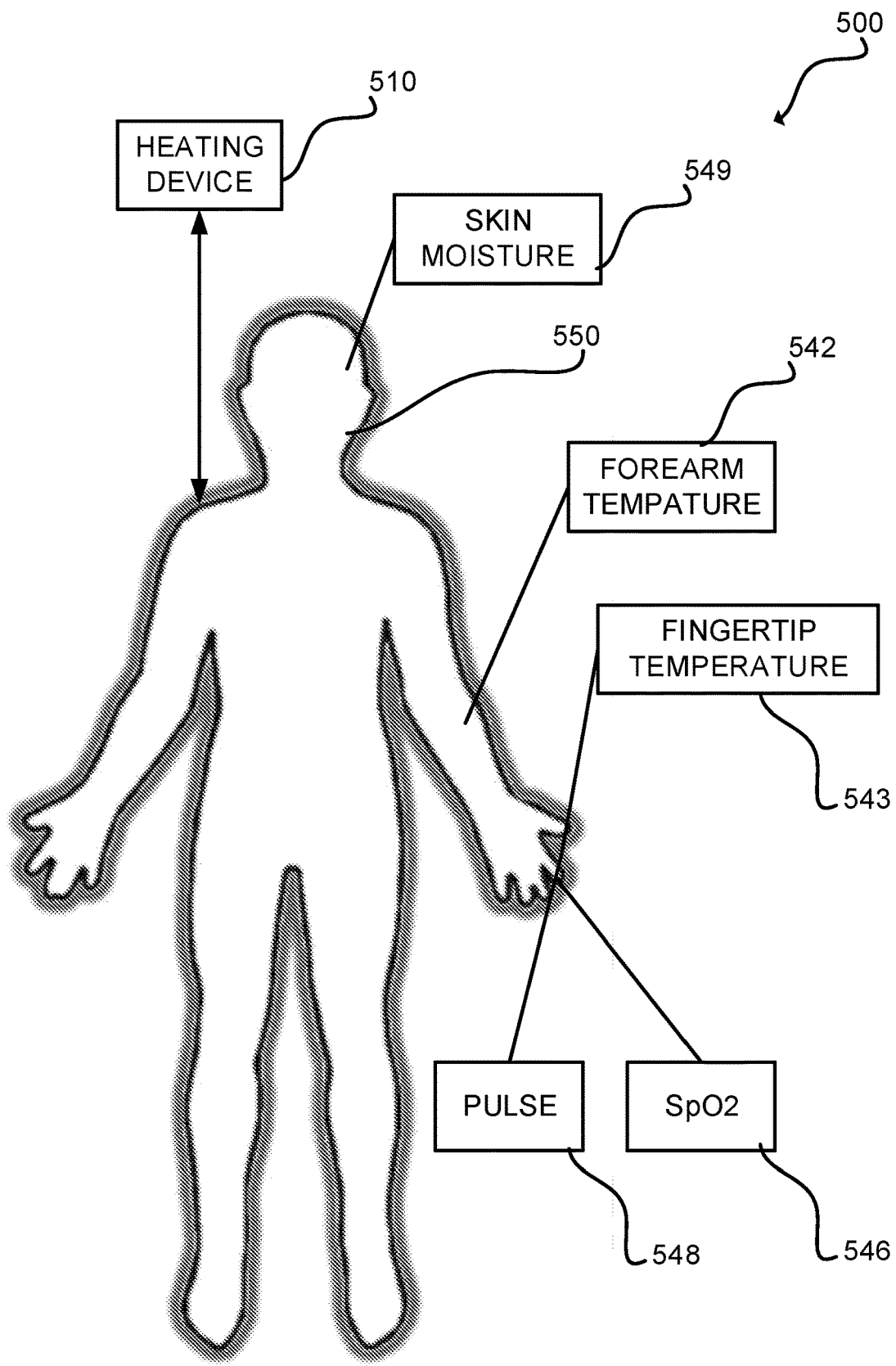
FIG. 8 illustrates a block diagram of a patient coupled to the one or more sensors, according to various techniques described in this disclosure.

FIG. 8 illustrates a patient warming system 500. The patient warming system 500 can be similar to patient warming system 100 in FIG. 1 with similarly numbered components except that various physiological indicators are shown in greater detail.

In the system 500, the heating device 510 can transfer heat to a patient 550 similar to heating device 110 in FIG. 1. The heating device 510 can have one or more sensors (not shown) similar to sensors 140 in FIG. 1.

The sensors (not shown) can measure certain physiological indicators such as skin moisture 549, forearm temperature 542, fingertip temperature 543, SpO2 546, Pulse 548.

The skin moisture 549 can be measured from a skin moisture sensor (not shown). The skin moisture 549 of a patient can be collected from the forehead of the patient. Some exemplary skin moisture 549 values that are indicative of sweating include a skin moisture level of above 40%.

The forearm temperature 542 and fingertip temperature 543 can be measured using a temperature sensor. The forearm temperature 542 can be measured from the forearm of a patient. In particular, the forearm temperature can be measured from the midpoint between a wrist bone of a patient and the elbow of a patient. In at least one embodiment, the forearm temperature 542 can be measured from the volar aspect of the forearm.

The fingertip temperature 543 can be measured from the tip of the finger of a patient, e.g., an index finger. In at least one embodiment, the fingertip temperature can be used in conjunction with at least one temperature measurement, e.g., a core body temperature. For example, if using a fingertip temperature and the core body temperature, the difference under normothermia can be no greater than 13° C. If the core body temperature does not change beyond +/−1% and the fingertip temperature is above 35° C., then the score may be higher causing the controller to deactivate the heating circuit. If the core body temperature does not change and when fingertip temperature is decreased to below 33° C., the score may be higher.

In at least one embodiment, the difference between the forearm temperature 542 and the fingertip temperature 543 can be an indication of sweating. For example, the difference under normothermia is about 4° C. As a patient undergoes sweating, the difference can decrease. For example, a difference of no greater than 2° C., or no greater than 1° C. can indicate that the patient is about to sweat. In another example, the difference can be relative to a baseline temperature obtained before the patient has undergone external heating. For example, the patient that has a temperature difference of no greater than 10%, no greater than 15%, or no greater than 20% of the baseline can likely sweat.

The SpO2 546 of the patient 550 can be a measure of the oxygen concentration within the blood of the patient. An oxygen concentration of less than 96% can indicate that the patient is likely to sweat especially when accompanied by a blood pressure drop. In at least one embodiment, the SpO2 546 can be used with fingertip temperature 543 to create a score. For example, under normothermia the SpO2 546 of a patient can be about 97% and the fingertip temperature 543 can be around 24° C. If the SpO2 546 decreases below 95%, below 94%, or below 93%, and the fingertip temperature 543 increases to above 30° C., above 31° C., above 32° C., above 33° C., above 34° C., or above 35° C., then the score can be increased.

The pulse 548 of the patient 550 can be a measure of the pulse rate of a patient 550. The pulse 548 can be compared to a resting pulse 548. A pulse 548 that is at least 20% over the resting pulse 548 can indicate that the patient 550 is likely to sweat.

Figure 9A:
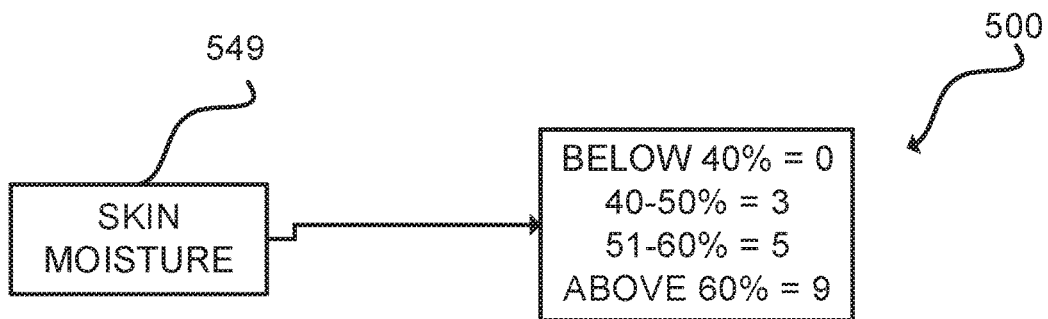
FIGS. 9A-9C illustrates a block diagram of an exemplary method for determining one or more physiological scores, according to various techniques described in this disclosure.
Figure 9B:
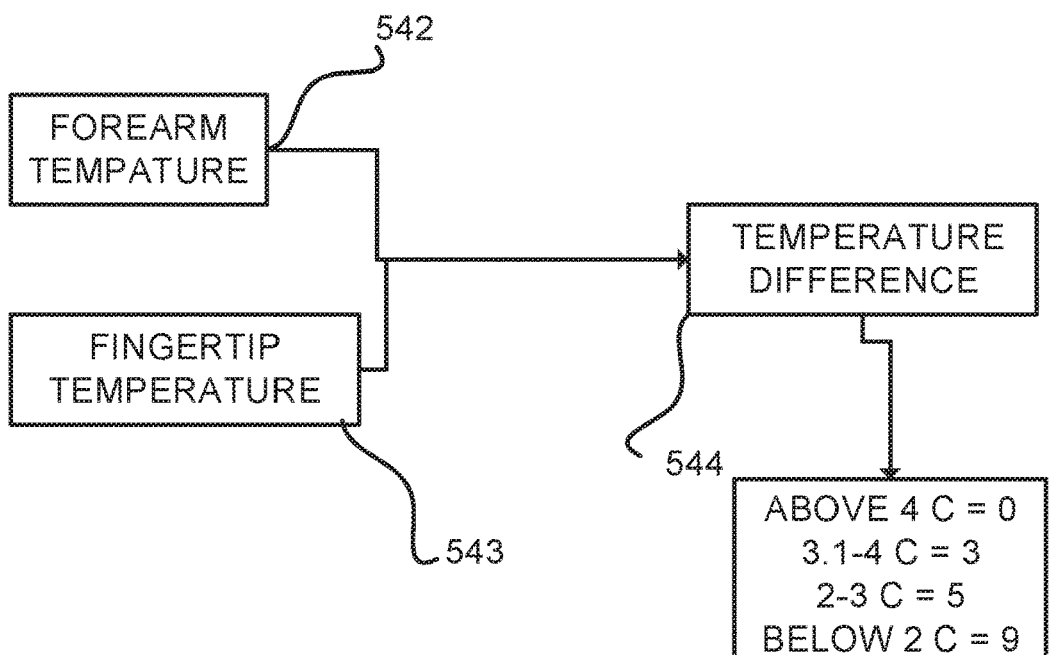
Figure 9C:
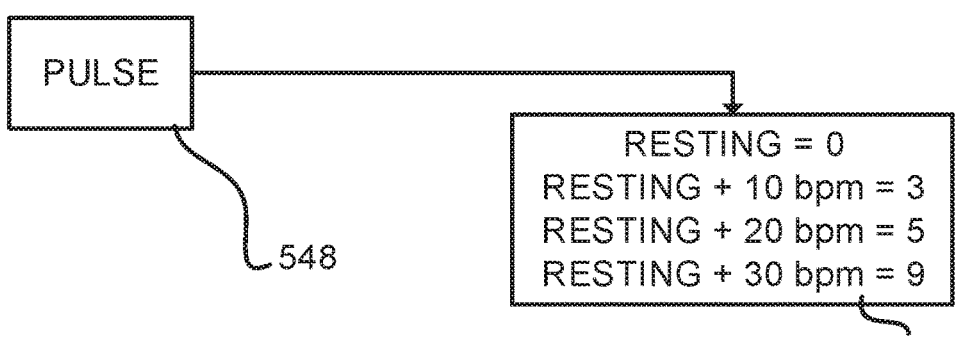

In FIGS. 9A-9C, an exemplary body heat score determination is demonstrated from some of the data collected from the system 500 in FIG. 7. The scoring performed by the controller in FIGS. 9A-C can be a lookup table where certain criteria observed by the controller will produce a certain physiological score.

In FIG. 9A, the skin temperature 549 can be measured by a sensor. For example, if the skin temperature 549 of the patient 550 is 55%, then controller can determine from the reference table 510 that the physiological score is 5.

In FIG. 9B, the forearm temperature 542 and fingertip temperature 543 can be measured by a temperature sensor. In at least one embodiment, the forearm temperature 543 or the fingertip temperature 543 can be used to determine a physiological score. In at least one embodiment, the forearm 543 fingertip 543 temperature difference can be scored in block 544. If the difference is determined to be 3.5° C., then the reference table 512 can be used to assign a physiological score of 3.

In FIG. 9C, the pulse 548 can be recorded by a pulse sensor or SpO2 sensor. The pulse 548 can indicate whether a patient 550 is likely to sweat. For example, an increasing pulse 548 can indicate that the patient 550 is removing excess body heat through sweat or eccrine glands. If the pulse 548 is 30 bpm above resting, then the reference table 514 can determine that the physiological score is 9.

Taken in the aggregate, an exemplary body heat score can be determined to be 5+3+9=17. If the score threshold is 14, then the score threshold is met and the heat from the heating device 510 can be reduced or stopped.

Figure 10A:
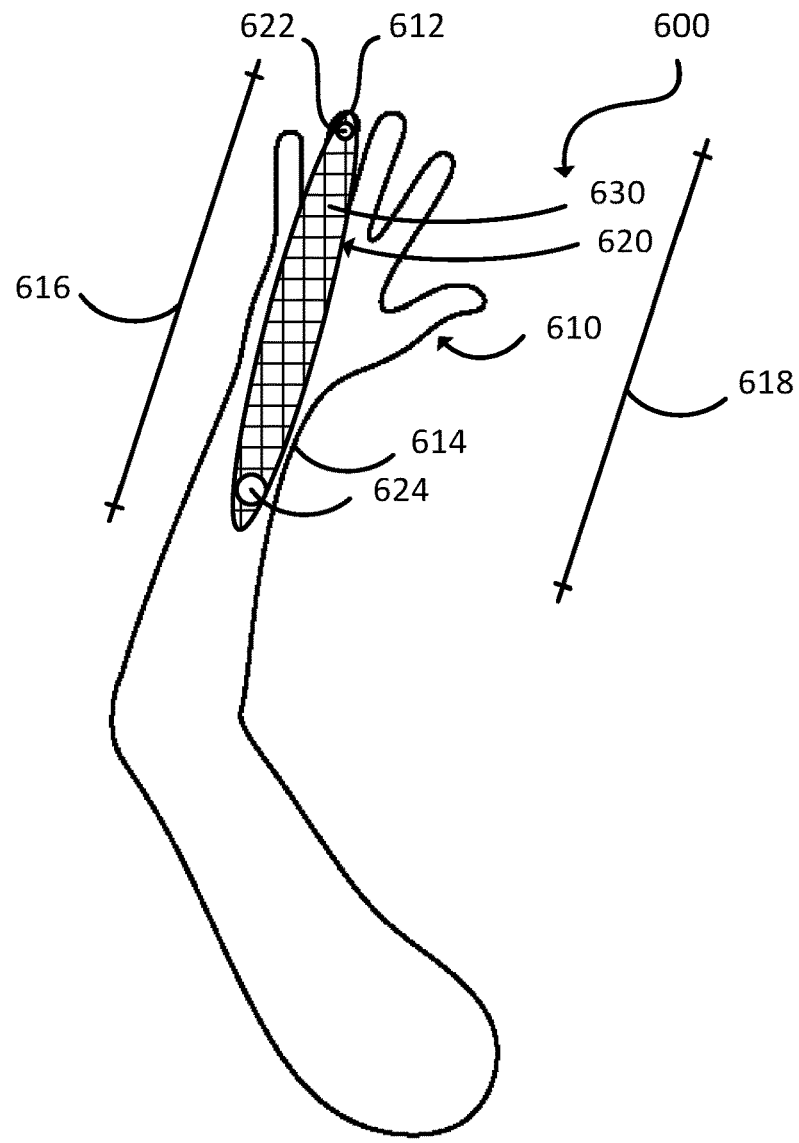
FIG. 10A-B illustrates a schematic diagram of a temperature monitoring device, according to various techniques described in this disclosure.
Figure 10B:
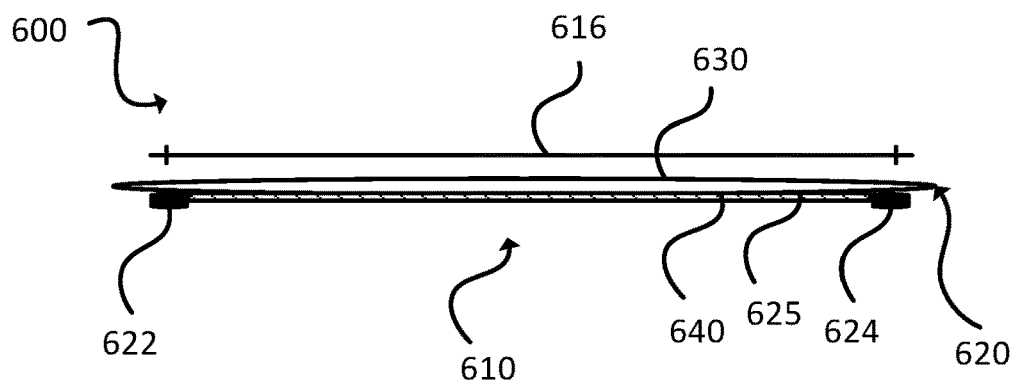

FIG. 10A-B illustrate a temperature monitoring device 600, according to various embodiments. The temperature monitoring device 600 can be configured to attach two temperature sensors 622, 624 to a patient arm 610. The patient arm 610 is shown from the volar surface. The patient arm 610 can have a particular spacing 618 between a fingertip 612 (shown on a ring finger) and a forearm 614. In particular the fingertip 612 can be a distal interphalangeal joint. The spacing 618 may vary from patient to patient and vary depending on which finger is used.

In at least one embodiment, a first temperature sensor 622 is disposed on the fingertip 612 and maintains a consistent spacing 616 relative to a second temperature 624 sensor disposed on the forearm 614 such that both the temperature of the forearm 614 and the fingertip 612 can be measured simultaneously. In at least one embodiment, the spacing 616 can be based on an average population length of ring fingertip to forearm. For example, the spacing 616 can be from 22-28 cm, or 24-26 cm.

The temperature monitoring device 600 can have a cover layer 620. The cover layer 620 can be a non-woven, woven (such as cloth), or other polymer. An example of the cover layer 620 can be available under the trade designation Micropore from 3M (St. Paul, MN). The cover layer 620 can have a first face 630 which can face outward. The first face 630 may further be coated with a polymer to improve the water resistance and durability.

In FIG. 10B, the cover layer 620 is shown with a second face 625. The second face 625 may face toward the arm 610. In at least one embodiment, the adhesive 640 can be disposed on a portion of the second face 625. The temperature sensors 622 and 620 can be disposed on either the second face 625 or the adhesive 640.

Figure 11:
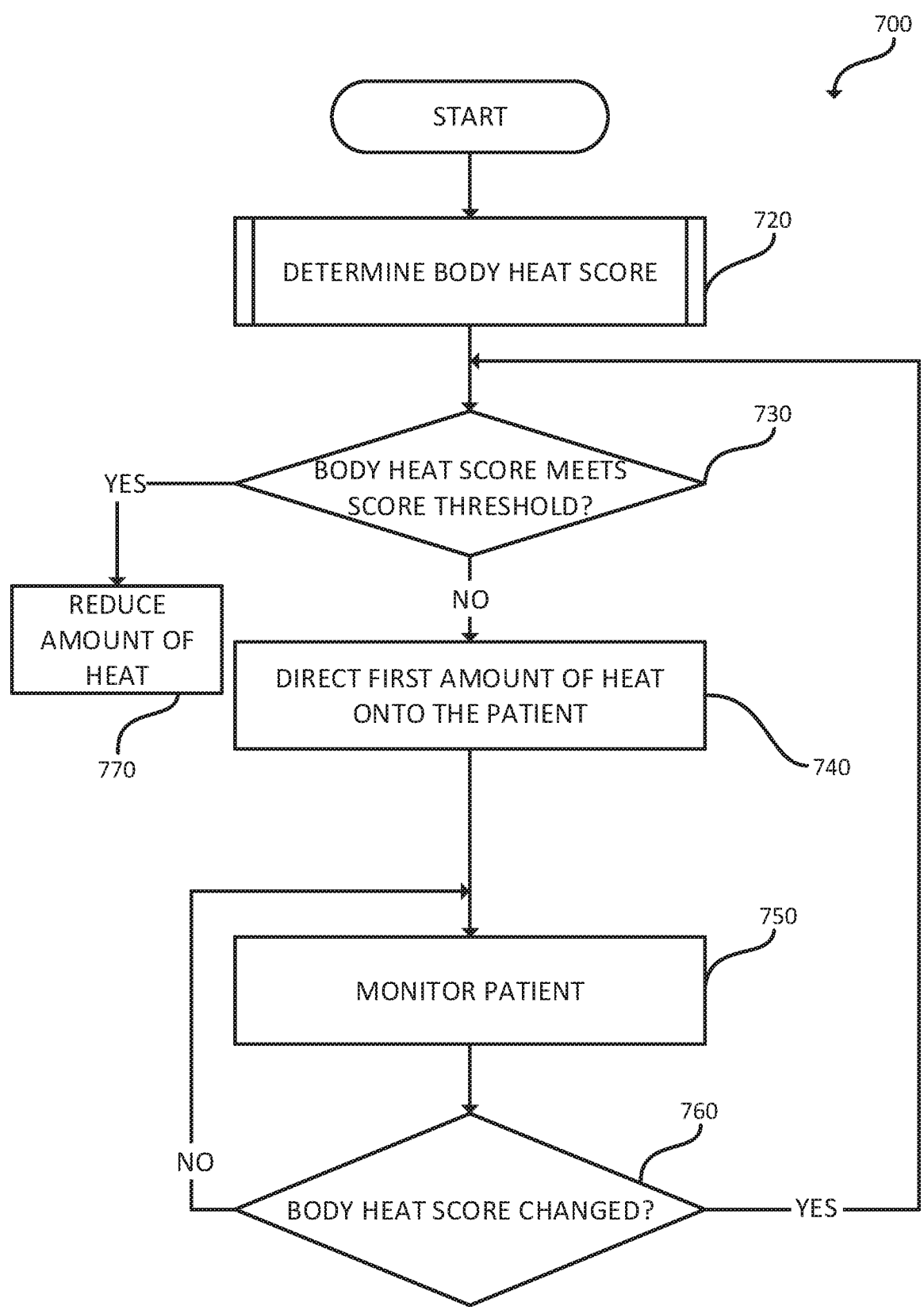
FIG. 11 illustrates a flowchart of an embodiment of a method for applying heat to a patient, according to various techniques described in this disclosure.

FIG. 11 illustrates a flowchart of an embodiment of a method 700 for applying heat to a patient, according to various techniques described in this disclosure. In at least one embodiment, the method 700 can be an alternate embodiment of method 200 in FIG. 5

In the method 700, the controller can determine an initial body heat score in block 720 based on physiological indicators such as those determined in method 400 in FIG. 7 or 171 in FIG. 4. Preferably, the physiological indicators used to determine the initial body heat score can be entered and based off of a patient's initial vital signs.

In block 730, the controller can determine if the body heat score meets the score threshold. For example, the score threshold can include whether the starting parameters for timed patient warming are met (e.g., a time condition). The score threshold can be met block 730 if the patient is undergoing thermogenesis such as feverish conditions. In which case, the controller reduces the amount of heat or stops the heater circuit in block 770.

In block 740, the controller can direct the first amount of heat onto the patient 740 (which is similar to block 230 in FIG. 5) and monitor the patient in block 750 (which is similar to block 270 in FIG. 5).

In block 760, the controller can determine if the body heat score has changed (e.g., through the one or more sensors. If the body heat score has changed, then the method 700 continues to block 730.

LIST OF ILLUSTRATIVE EMBODIMENTS

Embodiment A1

A method comprising:

determining a first amount of heat to transfer to a patient; and directing the first amount of heat to the patient.

Embodiment A2

The method of Embodiment A1, further comprising:

determining a body heat content of the patient based on one or more physiological indicators; and determining whether first amount of heat is sufficient for the patient to increase body heat content without sweating.

Embodiment A3

The method of Embodiment A1 or A2, further comprising:
  reducing an amount of heat directed onto the patient in response to the amount of heat being sufficient; and
  monitoring one or more physiological indicators of the patient.

Embodiment A4

The method of any of Embodiments A1-A3, further comprising:
  determining a second amount of heat to transfer to the patient;
  directing the second amount of heat to the patient.

Embodiment A5

The method of any of Embodiments A2-A4, wherein determining body heat content of the patient comprises:
  measuring a first set of one or more physiological indicators from a patient;
  determining a first physiological score from the first set of one or more physiological indicator; and
  determining a body heat score from one or more physiological scores.

Embodiment A6

The method of any of Embodiments A2-A5, wherein determining whether an amount of heat is sufficient comprises determining whether a score threshold is met by the body heat score.

Embodiment A7

The method of any of Embodiments A3-A6, wherein reducing an amount of heat directed onto the patient comprises turning off a heater circuit.

Embodiment A8

The method of any of Embodiments A1-A7, wherein at least one of the physiological indicators is a SpO2 measurement from the patient.

Embodiment A9

The method of any of Embodiments A1-A7, wherein at least one of the physiological indicators is a pulse from the patient.

Embodiment A10

The method of any of Embodiments A1-A7, wherein at least one of the physiological indicator is a skin electrical resistance or impedance.

Embodiment A11

The method of any of Embodiments A1-A7, wherein at least one of the physiological indicators is a temperature from the patient.

Embodiment A12

The method of Embodiment A11, wherein the temperature is measured from a fingertip of the patient.

Embodiment A13

The method of Embodiment A11, wherein the temperature is measured from a portion of a volar aspect of a forearm of the patient, wherein the forearm is between an elbow joint and a wrist joint of the patient.

Embodiment A14

The method of Embodiment A13, wherein a first physiological indicator is a fingertip temperature and a second physiological indicator is a forearm temperature.

Embodiment A15

The method of Embodiment A14, wherein the forearm temperature is measured on the volar aspect and on a midpoint between the elbow joint and a wrist joint of the patient.

Embodiment A16

The method of any of Embodiments A1-A14, wherein a first physiological indicator is a temperature of a pad of a finger between a distal interphalangeal joint and a distal end of a finger and a second physiological indicator is a temperature measured from a portion of the patient different from the fingertip.

Embodiment A17

The method of Embodiment A16, wherein a portion of the patient is selected from a group consisting of: a palm, a wrist, a different finger of the patient, another portion of the finger, core body temperature, and combinations thereof.

Embodiment A18

The method of Embodiment A17, wherein the core body temperature of the patient is measured from a zero-flux temperature sensor.

Embodiment A19

The method of any of Embodiments A1-A14, wherein the physiological indicator is a temperature difference between the first physiological indicator and the second physiological indicator.

Embodiment A20

The method of Embodiment A11, wherein the temperature is a body core temperature.

Embodiment A21

The method of any of Embodiments A1-A20, wherein the first amount of heat is applied to at least 30% of a total surface area of the patient.

Embodiment A22

The method of any of Embodiments A1-A21, wherein the first amount of heat is applied via convective heating.

Embodiment A23

The method of any of Embodiments A1-A22, wherein the first amount of heat is applied via conductive heating.

Embodiment A24

The method of any of Embodiments A5-A23, wherein the first score and the second score are an aggregate of the one or more physiological indicators.

Embodiment A25

The method of any of Embodiments A1-A24, wherein determining a first amount of heat to apply to the patient comprises:
receiving one or more physiological indicators relevant to thermolysis and thermogenesis of the patient;
determining a time condition based on the one or more physiological indicators;
determining whether the time condition is met.

Embodiment A26

The method of Embodiment A25, further comprising applying the second amount of heat to the patient based on the time condition being met.

Embodiment A27

The method of Embodiment A25, wherein determining a time condition further comprises determining a specific heat of the patient.

Embodiment B1

A system, comprising:
a heating device, wherein the heating device is configured to transfer heat to the patient sufficient to increase a body heat content of the patient without causing the patient to sweat, the heating device comprising:
a heater circuit configured to produce heat, the heater circuit thermally coupled to the patient;
a controller communicatively coupled to the one or more sensors and the heating device, the controller comprising:
a memory; and
one or more processors communicatively coupled to the memory configured to:
receive one or more entered physiological indicators of the patient;
determine the body heat content of the patient based on the one or more entered physiological indicators of the patient;
determine a first amount of heat to transfer to the patient based on the body heat content of the patient; and
direct the heater circuit to produce a first amount of heat.

Embodiment B2

The system of Embodiment B1, further comprising:
one or more sensors, wherein at least one of the one or more sensors is communicatively coupled to a patient;
wherein the one or more processors are configured to:
determine a body heat content of the patient from one or more physiological indicators received from the one or more sensors; and
determine whether first amount of heat is sufficient for the patient to increase body heat content without sweating.

Embodiment B3

The system of Embodiment B1 or B2, wherein the one or more processors are configured to:
determine a second amount of heat to transfer to the patient in response to the amount of heat not being sufficient;
direct the heater circuit to produce a second amount of heat.

Embodiment B4

The system of any of Embodiments B1-B3, wherein the one or more processors are configured to:
reduce an amount of heat directed onto the patient in response to the first amount of heat being sufficient; and
monitor one or more sensors for one or more physiological indicators from the patient.

Embodiment B5

The system of any of Embodiments B1-B4, wherein the one or more processors are configured to determine a body heat content of the patient by:
receiving a first set of one or more physiological indicators from the one or more sensors;
determining a first physiological score from the first set of one or more physiological indicators;
determining a body heat score from one or more physiological scores.

Embodiment B6

The system of any of Embodiments B1-B5, wherein the one or more processors are configured to determine whether a first amount of heat is sufficient by determining whether a body heat score meets the score threshold.

Embodiment B7

The system of any of Embodiments B1-B6, wherein the one or more processors are configured to turn off the heater circuit in response to the score threshold being met.

Embodiment B8

The system of any of Embodiments B1-B7 wherein directing the heater circuit to produce a second amount of heat occurs in response to the score threshold not being met.

Embodiment B9

The system of any of Embodiments B1-B8, further comprising: a heat transfer device, wherein the heat transfer device dissipates at least some of the heat over an area to the patient.

Embodiment B10

The system of Embodiment B9, wherein the heat transfer device is a convective warming blanket.

Embodiment B11

The system of Embodiment B9, wherein the heat transfer device is a conductive warming pad.

Embodiment B12

The system of Embodiment B9, wherein the heat transfer device is a stent.

Embodiment B13

The system of any of Embodiments B1-B12, wherein directing the heating circuit to produce the first amount of heat comprises:
  determining heating circuit settings relating to the first amount of heat, wherein the heating circuit settings includes a time condition; and
  determining whether the time condition is met.

Embodiment B14

The system of any of Embodiments B1-B13, wherein the entered physiological indicator is a physiological condition that is measured no more than 2 times per hour.

Embodiment B15

The system of any of Embodiments B1-B14, wherein the entered physiological indicator is selected from a group consisting of: age, height, weight, BMI, gender, body fat percentage, and combinations thereof.

Embodiment B16

The system of any of Embodiments B1-B15, wherein the physiological indicator measured from the sensor is measured more than 2 times per hour.

Embodiment B17

The system of any of Embodiments B1-B16, wherein the sensor is selected from a group consisting of: an SpO2 sensor, a temperature sensor, a pulse sensor, a blood pressure sensor, a moisture sensor, a heat flux sensor, or combinations thereof.

Embodiment B18

The system of any of Embodiments B1-B17, wherein the one or more processors is configured to determine whether vasodilation has occurred in the patient using the one or more physiological indicators from the sensor.

Embodiment B19

The system of Embodiment B18, wherein the sensor is a blood pressure sensor and a decrease of a blood pressure corresponds to vasodilation.

Embodiment C1

A system, comprising:
  one or more sensors, wherein at least one of the one or more sensors is communicatively coupled to a patient;
  a heating device, wherein the heating device is configured to transfer heat to the patient sufficient to increase a body heat content of the patient without causing the patient to sweat, the heating device comprising:
  a heater circuit configured to produce heat, the heater circuit thermally coupled to the patient;
  a controller communicatively coupled to the one or more sensors and the heating device, the controller comprising:
  a memory; and
  one or more processors communicatively coupled to the memory configured to:
    determine a first amount of heat to transfer to a patient;
    direct the heater circuit to produce a first amount of heat;
    determine a body heat content of the patient from one or more physiological indicators received from the one or more sensors; and
    determine whether the first amount of heat is sufficient for the patient to increase body heat content without sweating.

Embodiment C2

The system of Embodiment C1, wherein determining whether the first amount of heat is sufficient comprises:
  determining whether vasodilation has occurred in the patient using the one or more physiological indicators from the sensor.

Embodiment C3

The system of Embodiment C1 or C2, wherein the one or more processors are configured to:
  reduce an amount of heat directed onto the patient in response to the first amount of heat being sufficient; and
  monitor one or more sensors for one or more physiological indicators from the patient.

Embodiment C4

The system of any of Embodiments C1-C3, wherein the one or more processors are configured to determine a body heat content of the patient by:
  receiving a first set of one or more physiological indicators from the one or more sensors;
  determining a first physiological score from the first set of one or more physiological indicators;
  determining a body heat score from one or more physiological scores.

Embodiment C5

The system of Embodiment C6, wherein the one or more processors are configured to determine whether a first amount of heat is sufficient by determining whether a body heat score meets the score threshold.

Embodiment C6

The system of any of Embodiments C1-05, wherein the one or more processors are configured to turn off the heater circuit in response to the score threshold being met.

Embodiment C7

The system of any of Embodiments C1-C6, wherein the sensor is selected from a group consisting of: an SpO2 sensor, a temperature sensor, a pulse sensor, a blood pressure sensor, a moisture sensor, a heat flux sensor, or combinations thereof.

Embodiment C8

The system of any of Embodiments C1-C7, wherein the one or more processors is configured to determine whether vasodilation has occurred in the patient using the one or more physiological indicators from the sensor.

Embodiment C9

The system of Embodiment C8, wherein the sensor is a blood pressure sensor and a decrease of a blood pressure corresponds to vasodilation.

Embodiment C10

The system of any of Embodiments C1-C9, wherein at least one of the physiological indicators is a temperature from the patient.

Embodiment C11

The system of Embodiment C10, wherein the temperature is measured from a fingertip of the patient.

Embodiment C12

The system of Embodiment C11, wherein the temperature is measured from a portion of a volar aspect of a forearm of the patient, wherein the forearm is between an elbow joint and a wrist joint of the patient.

Embodiment C13

The system of Embodiment C12, wherein a first physiological indicator is a fingertip temperature and a second physiological indicator is a forearm temperature.

Embodiment C14

The system of Embodiment C12 or C13, wherein the forearm temperature is measured on the volar aspect and on a midpoint between the elbow joint and a wrist joint of the patient.

Embodiment C15

The system of any of Embodiments C12-C14, wherein a first physiological indicator is a temperature of a pad of a finger between a distal interphalangeal joint and a distal end of a finger and a second physiological indicator is a temperature measured from a portion of the patient different from the fingertip.

Embodiment C16

The method of Embodiment C15, wherein a portion of the patient is selected from a group consisting of: a palm, a wrist, a different finger of the patient, another portion of the finger, core body temperature, and combinations thereof.

Embodiment D1

A temperature measuring device comprising:
a cover layer;
a first temperature sensor and a second temperature sensor adjacent to a portion of the cover layer;
an adhesive disposed on the cover layer;
wherein the first temperature sensor and the second temperature sensor have a spacing such that both the temperature of a forearm and a fingertip of a patient can be measured simultaneously.

Embodiment D2

The temperature measuring device of Embodiment D1, wherein the spacing is based on an average population length of a ring fingertip to a forearm.

Embodiment D3

The temperature measuring device of Embodiment D1 or D2, wherein the spacing ranges from 22 to 28 cm (inclusive).

Embodiment D4

The temperature measuring device of Embodiment D3, wherein the spacing ranges from 24-26 cm (inclusive).

Embodiment D5

The temperature measuring device of any of Embodiments D1-D4, wherein the cover layer comprises a first face and a second face.

Embodiment D6

The temperature measuring device of Embodiment D5, wherein the first face is coated with a polymer.

Embodiment D7

The temperature measuring device of Embodiment D5 or D6, wherein the adhesive is disposed on a portion of the second face.

Embodiment D8

The temperature measuring device of any of Embodiments D5-D7, wherein the second face faces toward the arm of a patient.

Embodiment D9

The temperature measuring device of any of Embodiments D5-D8, wherein the first and second temperature sensor are disposed on the first face.

Embodiment D10

The temperature measuring device of any of Embodiments D5-D8, wherein the first and second temperature sensor are disposed on the adhesive.

Embodiment D11

The temperature measuring device of any of Embodiments D1-D10, wherein the cover layer is a non-woven. first and second temperature sensor are disposed on the adhesive.

Embodiment E1

A system, comprising:
a heating device, wherein the heating device is configured to transfer heat to a patient based on a body heat score that indicates whether the patient is likely to sweat, the heating device comprising:
a heater circuit configured to produce heat, the heater circuit thermally coupled to the patient;
a controller communicatively coupled to the heating circuit, the controller comprising:
one or more processors configured to:
receive one or more physiological indicators of the patient;
determine the body heat score from one or more physiological indicators;
determine whether the body heat score meets a score threshold;
direct the heater circuit to produce a first amount of heat based on whether the body heat score meets a score threshold.

Embodiment E2

The system of Embodiment E1, further comprising:
one or more sensors removably attached to the patient and communicatively coupled to the one or more processors, wherein the one or more sensors are configured to detect one or more physiological indicators of the patient;
wherein the one or more processors are configured to:
determine the body heat score of the patient from one or more physiological indicators received from the one or more sensors.

Embodiment E3

The system of Embodiment E1, wherein the one or more physiological indicators are entered physiological indicators.

Embodiment E4

The system of Embodiment E3, wherein an entered physiological indicator is selected from a group consisting of: age, height, weight, BMI, gender, body fat percentage, and combinations thereof.

Embodiment E5

The system of Embodiment E1, wherein the entered physiological indicator is a physiological condition that is measured no more than 2 times per hour.

Embodiment E6

The system of Embodiment E2, wherein the one or more processors are configured to:
reduce an amount of heat directed onto the patient in response to the first amount of heat being sufficient; and
monitor one or more sensors for one or more physiological indicators from the patient.

Embodiment E7

The system of Embodiment E1, wherein the one or more processors are configured to turn off the heater circuit in response to the score threshold being met.

Embodiment E8

The system of Embodiment E1, further comprising: a heat transfer device, wherein the heat transfer device dissipates at least some of the heat over an area to the patient.

Embodiment E9

The system of Embodiment E8, wherein the heat transfer device is a convective warming blanket.

Embodiment E10

The system of Embodiment E1, wherein directing the heating circuit to produce the first amount of heat comprises:
determining heater circuit settings relating to the first amount of heat, wherein the heating circuit settings includes a time condition; and
determining whether the time condition is met.

Embodiment E11

The system of Embodiment E10, wherein the one or more processors are configured to:
determine a second amount of heat to transfer to the patient if the body heat score does not meet the score threshold and the time condition is met;
direct the heater circuit to produce a second amount of heat.

Embodiment E12

The system of Embodiment E2, wherein a physiological indicator measured from the sensor is measured more than 2 times per hour.

Embodiment E13

The system of Embodiment E1, wherein the body heat score is an aggregate of one or more physiological scores; and
wherein one or more physiological scores is determined by a drop in a blood pressure measurement over a period of time.

Embodiment E14

The system of Embodiment E13, wherein one or more physiological scores is determined by a fingertip to forearm temperature differential.

What is claimed is:

1. A system configured to transfer heat to a patient, the system comprising:
   a heating device, configured to transfer heat to the patient based on a body heat score that indicates whether the patient is likely to sweat, the heating device comprising:
   a convective warming blanket;
   a heater circuit coupled with the convective warming blanket and configured to produce heat, the heater circuit including a heating level setting, a temperature setting, a pause period setting, and a time setting;
   a controller communicatively coupled to the heater circuit, the controller comprising a processor, comprising:
      a sensing component configured to receive one or more physiological indicators of the patient, wherein the physiological indicators comprise an entered physiological indicator from an input component and a measured physiological indicator from one or more sensors;
      a scoring component communicatively coupled to the sensing component and configured to:
         determine a physiological score from the physiological indicators;
         determine the body heat score from the one or more physiological scores;
         determine whether the body heat score meets a score threshold indicating that the patient is likely to sweat; and
         direct the heater circuit to produce a first amount of heat based on whether the body heat score meets the score threshold; and
      a timing component communicatively coupled to the heater circuit and the sensing component and configured to:
         determine a duration of heat transfer from the heating device to the patient, the duration beginning when the heat transfer begins and ending based on a time condition set by the time setting of the heater circuit, wherein the time condition is based on an estimate of an excessive amount of heat transferred to the patient; and
         determine when the measured physiological indicator is received by the sensing component.

2. The system of claim 1, wherein the one or more sensors are configured to be removably attachable to the patient and communicatively coupled to the processor, wherein the one or more sensors are configured to detect at least the measured physiological indicators.

3. The system of claim 1, wherein the entered physiological indicator is selected from the group consisting of age, height, weight, BMI, gender, body fat percentage, and combinations thereof.

4. The system of claim 1, wherein the entered physiological indicator comprises a physiological condition that is measured no more than 2 times per hour.

5. The system of claim 1, wherein the scoring component of the processor is configured to direct the heater circuit to produce a second amount of heat, which is less than the first amount of heat, based upon the body heat score meeting or exceeding the score threshold.

6. The system of claim 1, wherein the scoring component of the processor is configured to turn off the heater circuit in response to the body heat score meeting or exceeding the score threshold.

7. The system of claim 1, wherein the scoring component of the processor is configured to:
   determine a second amount of heat to transfer to the patient if the body heat score does not meet the score threshold and the time condition is met; and
   direct the heater circuit to produce the second amount of heat.

8. The system of claim 1, wherein the measured physiological indicator is measured from the one or more sensors more than two times per hour.

9. The system of claim 1, wherein the physiological score is determined by multiple measurements of the measured physiological indicator that indicate a drop in a blood pressure of the patient over a period of time measured by the timing component.

10. The system of claim 1, wherein the measured physiological indicator comprises a fingertip to forearm temperature differential.

11. The system of claim 1, wherein the measured physiological indicator comprises a measurement indicating whether vasodilation has occurred in the patient.

12. A system configured to transfer heat to a patient, the system comprising:
   a heating device, configured to transfer heat to the patient based on a body heat score that indicates whether the patient is likely to sweat, the heating device comprising:
   a convective warming blanket;
   a heater circuit coupled with the convective warming blanket and configured to produce heat, the heater circuit including a heating level setting, a temperature setting, a pause period setting, and a time setting;
   a controller communicatively coupled to the heater circuit, the controller comprising a processor, comprising:
      a sensing component configured to receive one or more physiological indicators of the patient, wherein the physiological indicators comprise an entered physiological indicator from an input component and a measured physiological indicator from one or more sensors;
      a scoring component communicatively coupled to the sensing component and configured to:
         determine a physiological score from the physiological indicators;
         determine the body heat score from the one or more physiological scores;
         determine whether the body heat score meets a score threshold indicating that the patient is likely to sweat; and
         direct the heater level setting of the heater circuit to produce a first amount of heat based on whether the body heat score meets the score threshold, wherein the first amount of heat is determined by the temperature setting; and
      a timing component communicatively coupled to the heater circuit and the sensing component and configured to:
         determine a duration of heat transfer from the heating device to the patient, the duration beginning when the heat transfer begins and ending based on a time condition set by the time setting of the heater circuit, wherein the time condition is based on an estimate of an excessive amount of heat transferred to the patient; and
         determine when the measured physiological indicator is received by the sensing component.

13. The system of claim 12, wherein the heater level setting is based on an amount of electrical current flowing through the heater circuit.

14. The system of claim 12, wherein the a scoring component is further configured to determine an amount of time that the heater circuit is spent in a pause period implemented by the pause setting of the heater circuit.

15. The system of claim 14, wherein the pause period comprises a time period where the heater circuit produces no heat.

* * * * *